United States Patent [19]

Matsuda et al.

[11] Patent Number: 5,696,097
[45] Date of Patent: Dec. 9, 1997

[54] ANTINEOPLASTIC 5'-DIACYLGLYCERYLPHOSPHATIDYL-2-DEOXY-2'-METHYLENYLCYTIDINES AND METHOD OF MAKING

[75] Inventors: Akira Matsuda, 12-1-7-501, Kita-24-Jo-Nishi, Kita-ku, Sapporo-shi, Hokkaido 001; Takuma Sasaki, 4-12-5-401, Izuminomachi, Kanazawa-shi, Ishikawa 921; Satoshi Shutou, Sapporo; Akihiro Fujii; Takashi Ono, both of Iruma; Shinji Sakata; Takanori Miyashita, both of Choshi, all of Japan

[73] Assignees: Yamasa Corporation, Chiba; Akira Matsuda, Hokkaido; Takuma Sasaki, Ishikawa, all of Japan

[21] Appl. No.: 525,606

[22] PCT Filed: Mar. 16, 1994

[86] PCT No.: PCT/JP94/00427

§ 371 Date: Sep. 15, 1995

§ 102(e) Date: Sep. 15, 1995

[87] PCT Pub. No.: WO94/21659

PCT Pub. Date: Sep. 29, 1994

[30] Foreign Application Priority Data

Mar. 18, 1993 [JP] Japan .................. 5-059060

[51] Int. Cl.$^6$ .................. A61K 31/70; C07H 19/207
[52] U.S. Cl. .................. 514/51; 435/89; 536/26.8; 536/28.52
[58] Field of Search .................. 536/26.8, 28.52; 514/51; 435/89

[56] References Cited

U.S. PATENT DOCUMENTS

| | | | |
|---|---|---|---|
| 3,472,837 | 10/1969 | Verheyden et al. | 536/27.14 |
| 4,471,113 | 9/1984 | MacCoss | 536/26.8 |
| 4,552,955 | 11/1985 | Takaku et al. | 536/27.11 |
| 4,921,951 | 5/1990 | Shuto et al. | 536/26.8 |
| 4,996,308 | 2/1991 | Edwards et al. | 536/27.14 |
| 4,997,924 | 3/1991 | Jarvi et al. | 536/27.14 |
| 4,997,925 | 3/1991 | Jarvi et al. | 536/27.14 |
| 5,223,263 | 6/1993 | Hostetler et al. | 424/450 |
| 5,378,693 | 1/1995 | McCarthy et al. | 536/27.14 |
| 5,470,837 | 11/1995 | Wolos et al. | 536/27.14 |
| 5,484,911 | 1/1996 | Hong et al. | 536/27.14 |
| 5,512,671 | 4/1996 | Piantadosi et al. | 536/26.1 |
| 5,521,162 | 5/1996 | Jarvi et al. | 536/27.14 |

FOREIGN PATENT DOCUMENTS

| | | |
|---|---|---|
| 262876 | 4/1988 | European Pat. Off. |
| 2-157292 | 6/1990 | Japan |
| 4-21694 | 1/1992 | Japan |

OTHER PUBLICATIONS

Shuto et al., "Nucleosides and Nucleotides. 155. Synthesis Antitumor Effect, and Possible Enzymatic Activation Mechanism of 5'-Phosphatidyl-2'-deoxy-2'-methylenecytidine (DMDC)," *Bioorganic & Medicinal Chem. Letters.* 6(18), 2177–2182 (1996).

Shuto et al., "A Facile One–Step Synthesis of 5'–Phosphatidylnucleosides by an Enzymatic Two–Phase Reaction," *Tetrahedron Letters*, 28(2), 199–202 (1987).

Matsuda et al., "Alkyl Addition Reaction of Pyrimidine 2'–Ketonucleosides: Synthesis of 2'–Branched–Chain Sugar Pyrimidine Nucleosides," *Chem. Pharm. Bull.* 36(3), 945–953 (1988).

Takenuki et al., "Design, Synthesis, and Antineoplastic Activity of 2'-Deoxy-2'-methylidenecytidine." *J. Med. Chem.*, 31(6), 1063–1064 (Jun. 1988).

Ryu et al., "Phospholipid–Nucleoside Conjugates. 3. Synthesis and Preliminary Biological Evaluation of 1–β–D–Arabinofuranosylcytosine–5'–Monophosphate–L–1,2–Dipalmitin and Selected 1–β–D–Arabinofuranosylcytosine–5'–Diphosphate–L–1,2–Diacylglycerols," *J. Medicinal Chem.*, 25(11), 1322–1329 (1988).

*Primary Examiner*—John Kight
*Assistant Examiner*—L. Eric Crane
*Attorney, Agent, or Firm*—Wenderoth, Lind & Ponack

[57] ABSTRACT

Novel 2'-methylidenenucleotide compounds of the formula (I)

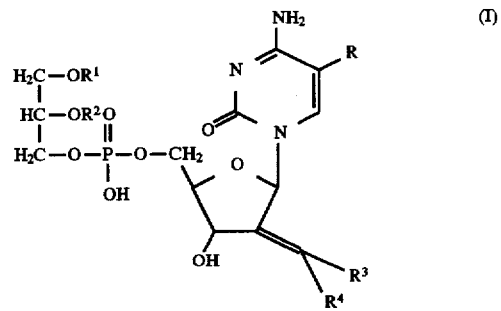

wherein R is a hydrogen or a halogen, $R^1$ and $R^2$ are the same or different and each is a fatty acid residue or a hydrocarbon residue, and $R^3$ and $R^4$ are the same or different and each is a hydrogen, a halogen or an alkyl; salts thereof; methods for production thereof; and pharmaceutical use thereof. The compounds and salts thereof show an excellent antitumor effect in mammals. More specifically, they show a remarkable activity of inhibiting growth of mouse tumors, cultured human tumor cells, and human tumors transplanted to nude mice, and are useful for the treatment and prevention of recurrence of lung cancer, gastrointestinal cancer, breast cancer, cervical cancer, gynecological cancer, urinological cancer, leukemia, melanoma, lymphogenous metastatic tumor and the like in mammals. They are also useful as antitumor agents since they have an increased bioavailability and low toxicity. In addition, they have the effects of maintaining and enhancing their activities.

10 Claims, No Drawings

ANTINEOPLASTIC 5'-DIACYLGLYCERYLPHOSPHATIDYL-2-DEOXY-2'-METHYLENYLCYTIDINES AND METHOD OF MAKING

BACKGROUND OF THE INVENTION

1. Field of the Invention

The present invention relates to novel 2'-methylidenenucleotide compounds and salts thereof having superior antitumor effect and useful as pharmaceuticals, methods for production thereof, pharmaceutical compositions comprising same as an effective ingredient and methods for treating tumor.

2. Description of Related Art

Nucleoside antitumor agents have been conventionally used for an extensive range of clinical situations against various tumors, but are associated with the following problems. That is, while the activity of said antitumor agents is expressed upon phosphorylation of 5'-position hydroxy, the agents are susceptible to decomposition into inactive substances by phosphorolysis, deamination and so on; the tumor cells come to have resistance to said antitumor agents; and the agents show toxicity to normal cells as well.

Hence, nucleoside antitumor agents free of these problems are desired.

An object of the present invention is to solve the above-mentioned problems and to provide novel 2'-methylidenenucleotide compounds superior to known nucleoside antitumor agents in properties, methods for production thereof and pharmaceutical use thereof.

SUMMARY OF THE INVENTION

The present inventors have conducted intensive studies in an effort to accomplish the aforementioned object, and found that novel 2'-methylidenenucleotide compounds of the formula (I) to be shown below and salts thereof have extremely superior properties.

The present invention has been completed based on the above finding, and relates to 2'-methylidenenucleotide compounds of the formula (I)

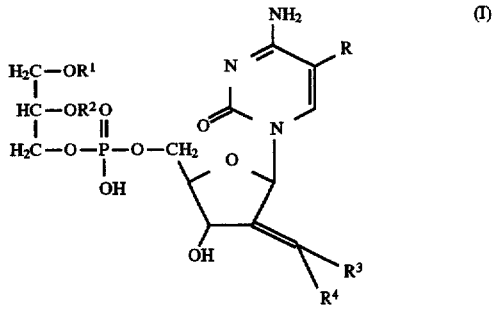

wherein

R is a hydrogen or a halogen;
$R^1$ and $R^2$ are the same or different and each is a fatty acid residue or a hydrocarbon residue; and
$R^3$ and $R^4$ are the same or different and each is a hydrogen, a halogen or an alkyl, and salts thereof.

Of the compounds of the formula (I), the present invention particularly relates to 2'-methylidenenucleotide compounds wherein R, $R^3$ and $R^4$ are each hydrogen, 2'-methylidene-nucleotide compounds wherein R is fluorine, and $R^3$ and $R^4$ are each hydrogen, 2'-methylidenenucleotide compounds wherein R, $R^3$ and $R^4$ are each hydrogen, and $R^1$ and $R^2$ are the same fatty acid residues, 2'-methylidenenucleotide compounds wherein R is fluorine, $R^3$ and $R^4$ are each hydrogen, and $R^1$ and $R^2$ are the same fatty acid residues, 2'-methylidenenucleotide compounds wherein R, $R^3$ and $R^4$ are each hydrogen, and $R^1$ and $R^2$ are the same fatty acid residues having 12 to 20 carbon atoms, 2'-methylidenenucleotide compounds wherein R is fluorine, $R^3$ and $R^4$ are each hydrogen, and $R^1$ and $R^2$ are the same fatty acid residues having 12 to 20 carbon atoms, and salts thereof.

The present invention also relates to methods for producing 2'-methylidenenucleotide compounds of the above-mentioned formula (I) and salts thereof, comprising reacting a phospholipid of the formula (II)

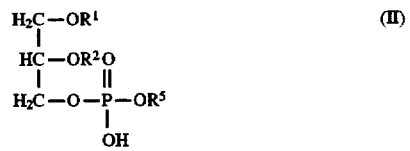

wherein $R^1$ and $R^2$ are as defined above, and $R^5$ is a choline residue, with a nucleoside of the formula (III)

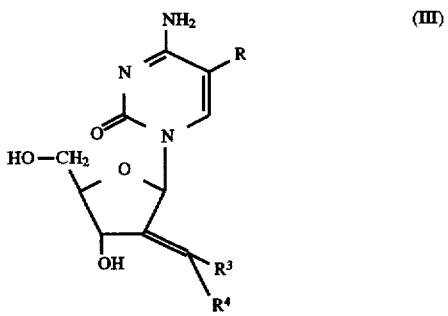

wherein R, $R^3$ and $R^4$ are as defined above, in the presence of a phospholipase D.

The present invention also relates to pharmaceutical compositions comprising a 2'-methylidenenucleotide compound of the aforementioned formula (I) or a salt thereof, and a pharmaceutically acceptable carrier. The present invention also relates to methods for treating tumor, comprising administering an effective amount of a 2'-methylidenenucleotide compound of the aforementioned formula (I) or a salt thereof to mammals inclusive of human in need of treating tumor.

DETAILED DESCRIPTION OF PREFERRED EMBODIMENT

(1) Compound

In the present specification, halogen represented by R, $R^3$ and $R^4$ means fluorine, chlorine, bromine and iodine.

The fatty acid residue represented by $R^1$ and $R^2$ means that having 2 to 30, preferably 10–24 and more preferably 12–20 carbon atoms, and may be a saturated fatty acid residue or an unsaturated fatty acid residue. Specific examples of the fatty acid residue include saturated fatty acid residues such as lauroyl, myristoyl, palmitoyl, stearoyl and icosanoyl, and unsaturated fatty acid residues having 1 to 4 unsaturated bonds, such as palmitoleoyl, oleoyl, linoleoyl, linolenoyl and arachidonoyl.

The hydrocarbon residue represented by $R^1$ and $R^2$ means that having 2 to 30, preferably 10–24 and more preferably 12–20 carbon atoms, and may be a saturated hydrocarbon residue or an unsaturated hydrocarbon residue. Specific examples of the hydrocarbon residue include saturated hydrocarbon residues such as lauryl, myristyl, palmityl, stearyl and icosanyl, and unsaturated hydrocarbon residues having 1 to 4 unsaturated bonds, such as palmitoleyl, oleyl, linoleyl, linolenyl and arachidonyl.

The alkyl represented by $R^3$ and $R^4$ means that having 1 to 5 carbon atoms, such as methyl, ethyl, propyl, isopropyl, butyl and pentyl.

The 2'-methylidenenucleotide compounds of the present invention show superior properties either in the form of salt or hydrate. Examples of such salt include addition salts with inorganic acid (e.g. hydrochloric acid, sulfuric acid, hydrobromic acid and phosphoric acid) or with organic acid (e.g. fumaric acid, tartaric acid, succinic acid, citric acid and methanesulfonic acid); salts with metal (e.g. sodium, potassium and calcium); and ammonium salt. When said salts are used for pharmaceutical compositions, it is desirable that they be pharmaceutically acceptable. Examples of hydrate include that wherein one molecule of a 2'-methylidenenucleotide compound of the present invention or a salt thereof is hydrated with 0.1–3 molecules of water. Isomers are also encompassed in the present invention.

Of such 2'-methylidenenucleotide compounds of the present invention, preferable compounds satisfy at least one of the following conditions ① to ⑬:

① R is hydrogen;

② R is fluorine;

③ $R^3$ and $R^4$ are the same and are each hydrogen or fluorine;

④ $R^3$ is hydrogen and $R^4$ is fluorine;

⑤ $R^3$ is fluorine and $R^4$ is hydrogen;

⑥ $R^1$ and $R^2$ are fatty acid residues;

⑦ $R^1$ and $R^2$ are the same saturated fatty acid residues;

⑧ $R^1$ and $R^2$ are the same unsaturated fatty acid residues;

⑨ $R^1$ and $R^2$ are hydrocarbon residues;

⑩ $R^1$ and $R^2$ are the same saturated hydrocarbon residues;

⑪ $R^1$ and $R^2$ are the same unsaturated hydrocarbon residues;

⑫ the compound is in the form of a salt; and

⑬ the compound is in the form of a hydrate.

(2) Production method

The 2'-methylidenenucleotide compounds of the present invention can be produced, for example, according to the following reaction scheme.

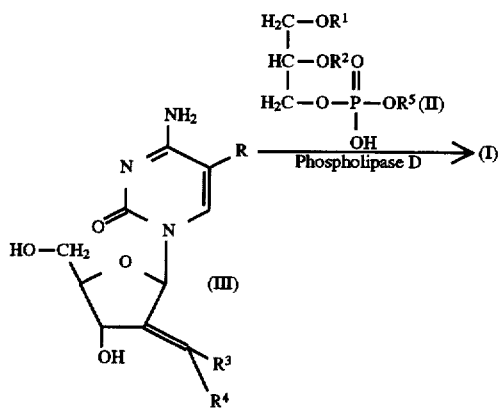

wherein R, $R^1$, $R^2$, $R^3$ and $R^4$ are as defined above and $R^5$ is a choline residue.

That is, the 2'-methylidenenucleotide compound of the present invention can be produced by reacting a phospholipid of the formula (II) with a nucleoside of the formula (III) in a solvent in the presence of a phospholipase D, in coexistence of metallic ion where necessary.

The phospholipid to be used in the method of the present invention includes, for example, phosphatidylcholine having the aforementioned $R^1$ and $R^2$, such as 1,2-diacyl-sn-glycero-3-phosphocholine, 1,2-dialkyl-sn-glycero-3-phosphocholine and 1,2-dialkenyl-sn-glycero-3-phosphocholine. These phosphatidylcholines are commercially available from reagent makers and can be used in the present invention. When $R^1$ and $R^2$ are fatty acid residues, naturally occurring phosphatidylcholine represented by a radyl group, which is a mixture of long chain fatty acids having 12 to 20 carbon atoms, can be also used.

The nucleoside to be used in the present method is represented by the above-mentioned formula (III) and preferable examples thereof include 2'-deoxy-2'-methylidenecytidine (EP-A-0310673, EP-A-0443471), 2'-deoxy-2'-methylidene-5-fluorocytidine (EP-A-0360018), 2'-deoxy-2'-difluoromethylidenecytidine, (E)-2'-deoxy-2'-fluoromethylidenecytidine and (Z)-2'-deoxy-2'-fluoromethylildenecytidine (the last three in EP-A-0372268).

The phospholipase D to be used in the present method is preferably exemplified by phospholipase D-P (Japanese Patent Unexamined Publication No. 152481/1983, commercially available from Asahi Chemical Industry Co., Ltd.) which is derived from Streptomyces sp. AA586; FERM P-6100 belonging to the genus Streptomyces. The amount to be used is 0.01 unit (unit: U) or above, preferably 0.1–100 units, per 1 mg of phosphatidylcholine.

The solvent to be used in the present method is exemplified by two layer solvents comprising organic solvent layer and aqueous solvent layer, such as organic solvents (e.g. ether, benzene and chloroform) and buffer solutions (pH 3–9, preferably pH 4–6).

A metallic ion may be present in a reaction mixture for promoting an enzyme reaction. For forming such metallic ion, a water soluble salt is used, which is generally exemplified by calcium chloride. The reaction temperature is generally 20°–60° C., and the reaction time of 30 minutes to 50 hours is sufficient.

The 2'-methylidenenucleotide compound of the present invention thus obtained can be purified by liquid separation, silica gel chromatography and the like.

The salt and hydrate of the 2'-methylidenenucleotide compound of the present invention can be produced and purified by a method known per se.

(3) Use

The 2'-methylidenenucleotide compounds and salts thereof of the present invention have superior antitumor effect in mammals such as human, mouse, rat, rabbit, dog, cat and the like. They are extremely useful as antitumor agents since they have an increased bioavailability and low toxicity.

That is, the 2'-methylidenenucleotide compounds and salts thereof of the present invention exhibit remarkable effect of inhibiting the growth of mouse tumors such as L1210 leukemia cells, P388 leukemia cells, M5076 sarcoma, B16 mouse melanoma, Lewis lung cancer and Colon 26 colon cancer; cultured human tumor cells (e.g. tumor cells from CEM acute T cell leukemia, U937 human tissue acute leukemia, MOLT4 acute T cell leukemia, K562 chronic myelocytic leukemia, SK-Mel-28 melanoma, T24 bladder cancer, TE2 esophageal gland cancer, SW colon gland cancer, KB epidermic cancer, Lu-65 lung large cell carcinoma, PC13 lung large cell carcinoma, PC14 lung gland cancer and KATOIII stomach cancer); and human tumors transplanted to nude mouse (e.g. tumors of SK-Mel-28 melanoma, LX-1 lung cancer, Lu116 lung cancer, PC10 lung cancer, PC14 lung cancer, MX-1 breast cancer and SC6 stomach cancer). They are useful for the treatment and prevention of recurrence of tumors in mammals inclusive of human, such as lung cancer, gastrointestinal cancers (e.g. esophageal cancer, stomach cancer, large intestin cancer, rectum cancer and colon cancer), breast cancer, cervical cancer, gynecological cancers (e.g. uterine cancer and ovarian cancer), urinological cancers (e.g. kidney cancer, bladder cancer), leukemia, melanoma, lymphogenous metastatic tumor and the like.

The 2'-methylidenenucleotide compounds and salts thereof of the present invention are advantageous in that they are highly liposoluble, so that they reside in the body for a long time while maintaining their activity; are not easily inactivated by deamination, phosphorolysis, reduction and the like; have high affinity for biomembranes; and allow intracellular production of 5'-monophosphoric acid compound of antitumor nucleoside without involvement of kinase. That is, the 2'-methylidenenucleotide compounds and salts thereof of the present invention have the effects of maintaining and enhancing their activities.

When the 2'-methylidenenucleotide compounds and salts thereof of the present invention are used as pharmaceuticals, an effective amount thereof is generally admixed with pharmacologically acceptable carrier, excipient, diluent and the like, and formulated into powder, granule, tablet, sugar-coated tablet, capsule, syrup, suppository, external agent, injection, transfusion and the like, with preferred form being an oral preparation.

While the dose varies depending on the target disease, administration route, dosage form and the like, the 2'-methylidenenucleotide compound or a salt thereof of the present invention is generally administered orally in a dose of 10–400 mg/kg body weight, preferably 50–200 mg/kg body weight per day, or in a dose of 1–10 mg/kg body weight, preferably 1–5 mg/kg body weight per day by injection. The administration frequency can be appropriately selected and is 1 to 4 times a day.

The present invention is described in more detail by way of Examples, to which the present invention is not limited.

EXAMPLE 1

2'-Deoxy-2'-methylidenecytidine dihydrate (120 mg, 0.05 mmol) was dissolved in 2.0M sodium acetate buffer (pH 4.5). Phospholipase D-P (PLDP) (3 mg, 522 U) and 1,2-dipalmitoyl-sn-glycero-3-phosphocholine (DPPC) (404 mg, 0.55 mmol) dissolved in 20 ml of chloroform were added, and the mixture was vigorously stirred at 45° C. PLDP (2 mg, 348 U) was added 2 hours later and 4 hours later, and the mixture was stirred for 6 hours in total. The reaction mixture was allowed to cool, and chloroform (20 ml), methanol (20 ml) and water (5 ml) were added to partition the mixture. The lower layer was washed 3 times with methanol-water (1:1, 10 ml), and the solvent was distilled away. The residue was dissolved in a small amount of chloroform-methanol (2:1) and adsorbed on silica gel, which was purified by silica gel column chromatography ($\phi$ 2.8 cm×7.5 cm+2.0 cm, eluted with 25% methanol/chloroform) to give a white solid. The solid was dissolved in chloroform-methanol-water (10:5:1) and the mixture was poured on Diaion WK-20 resin column (Na type, $\phi$ 2.2 cm×6.0 cm) and eluted with the same solvent, whereby 216 mg (0.24 mmol) of 5'-(1,2-dipalmitoyl-sn-glycero-3-phospho)-2'-deoxy-2'-methylidenecytidine sodium salt ½ hydrate was obtained, yield 48%.

Elemental analysis ($C_{45}H_{79}N_3O_{11}$ PNa . ½ $H_2O$); Calculated C: 58.80, H: 8.99, N: 4.57 Found C: 58.8.2, H: 8.94, N: 4.59

FAB-MS (m/z); 892 ($M^+$)

UV; $\lambda$max (MeOH, $OH^-$) 271 nm, $\lambda$max ($H^+$) 280 nm

NMR ($CDCl_3$—$CD_3OD$, 3:1) $\delta$; 7.82 (d, 1H, 6-H, $J_{6,5}$= 7.7 Hz), 6.67 (s, 1H, 1'-H), 6.00 (d, 1H, 5-H, $J_{5,6}$=7.3 Hz), 5.52 (br.s, 1H, 2'-C=CHa), 5.47 (br.s, 1H, 2'-C=CHb), 5.38–5.21 (m, 1H, glycerol 2-H), 4.79–4.76 (m, 1H, 3'-H), 4.41–3.82 (m, 7H, 4',5',5'-H, glycerol 1,3-H), 2.32 (t, 2H, $COCH_2$, J=7.7 Hz), 2.31 (t, 2H, $COCH_2$, J=7.7 Hz), 1.60 (m, 4H, $COCCH_2$), 1.26 (m, 48H, palmitoyl $CH_2$), 0.88 (t, 6H, palmitoyl $CH_3$, J=6.6 Hz)

EXAMPLE 2

2'-Deoxy-2'-methylidene-5-fluorocytidine (129 mg, 0.50 mmol) was dissolved in 2.0M sodium acetate buffer (pH 4.5). PLDP (3 mg, 522 U) and DPPC (404 mg, 0.55 mmol) dissolved in 20 ml of chloroform were added. The mixture was vigorously stirred at 45° C. PLDP (2 mg, 348 U) was added 2 hours later and 4 hours later, and the mixture was stirred for 6 hours in total. The reaction mixture was allowed to cool, and chloroform (20 ml), methanol (20 ml) and water (5 ml) were added to partition the mixture. The lower layer was washed 3 times with methanol-water (1:1, 10 ml), and the solvent was distilled away. The residue was dissolved in a small amount of chloroform-methanol (2:1) and adsorbed on silica gel, which was purified by silica gel column chromatography ($\phi$ 2.8 cm×8.0 cm+2.0 cm, eluted with 25% methanol/chloroform) to give a white solid. The solid was dissolved in chloroform-methanol-water (10:5:1) and the mixture was poured on Diaion WK-20 resin column (Na type, $\phi$ 2.2 cm×5.5 cm) and eluted with the same solvent, whereby 223 mg (0.25 mmol) of 5'-(1,2-dipalmitoyl-sn-glycero-3-phospho)-2'-deoxy-2'-methylidene-5-fluorocytidine sodium salt ½ hydrate was obtained, yield 49%.

Elemental analysis ($C_{45}H_{78}N_3O_{11}$ FPNa . ½ $H_2O$); Calculated C: 58.81, H: 8.66, N: 4.57 Found C: 58.72, H: 8.64, N: 4.40

FAB-MS (m/z); 910 ($M^+$)

UV; $\lambda$max (MeOH, $OH^-$) 271 nm, $\lambda$max ($H^+$) 280 nm

NMR ($CDCl_3$—$CD_3OD$, 3:1) $\delta$; 7.73 (d, 1H, 6-H, $J_{6,5F}$= 6.2 Hz), 6.65 (s, 1H, 1'-H), 5.53 (s, 1H, 2'-C=CHa), 5.47 (s, 1H, 2'-C=CHb), 5.24 (m, 1H, glycerol 2-H), 4.73 (m, 1H, 3'-H), 4.21–3.85 (m, 8H, 3',4',5'-H, glycerol 1,3-H), 2.36–2.28 (m, 4H, COCH$_2$), 1.60 (br.s, 4H, COCCH$_2$), 1.43–1.27 (m, 48H, palmitoyl CH$_2$), 0.89 (t, 6H, palmitoyl CH$_3$) In Examples 3 to 8, the following method was used.

2'-Deoxy-2'-methylidenecytidine dihydrate (1.9–3.5 g, 7–12.5 mmol) and calcium chloride dihydrate (1.4 g) were dissolved in purified water (40 ml). The pH of the mixture was adjusted to 4.3–4.5 with 1N hydrochloric acid. PLDP (1–4 mg, 180–720 U) and phosphatidylcholine (0.7–2.9 mmol) dissolved in 80 ml of chloroform were added, and the mixture was vigorously stirred at 35°–40° C. for 3–8 hours. The reaction mixture was partitioned between chloroform (53 ml) and methanol (67 ml), and the lower layer was washed by adding methanol (67 ml) and water (40 ml). The solvent was distilled away. The residue was dissolved in a small amount of chloroform-methanol (2:1) and adsorbed on silica gel, which was purified by silica gel column chromatography (elated with chloroform:methanol=3:1) to give a white solid. The solid was dissolved in a chloroform:methanol (2:1) solution (180 ml) and the mixture was partitioned from 0.75N hydrochloric acid (27 ml). Water (27 ml) and methanol (30 ml) were added to the lower layer to partition same (3 times), and methanol (30 ml) was added. The mixture was poured on Diaion WK-20 resin column (Na type) and eluted with chloroform-methanol-water (10:5:1). The solvent was distilled away and acetone was added to the residue to give a powdery object compound.

EXAMPLE 3

5'-(1,2-Distearoyl-sn-glycero-3-phospho)-2'-deoxy-2'-methylidenecytidine Sodium Salt Using 2.0 g (2.5 mmol) of 1,2-distearoyl-sn-glycero-3-phosphocholine (DSPC) as phosphatidylcholine, a powdery object compound (1.7 g) was synthesized according to the above-mentioned method, yield 72%.

Elemental analysis (C$_{49}$H$_{87}$N$_3$O$_{11}$PNa) Calculated C: 62.07, H: 9.25, N: 4.43 Found C: 61.81, H: 9.47, N: 4.53

NMR (CDCl$_3$—CD$_3$OD, 3:1) δ; 7.79 (d, 1H, 6-H, J$_{5,6}$=7.3 Hz), 6.69 (s, 1H, 1'-H), 5.98 (d, 1H, 5-H, J$_{5,6}$=7.3 Hz), 5.51 (s, 1H, —C=CHa), 5.47 (s, 1H, —C=CHb), 5.24–5.22 (m, 1H, glycerol 2-H), 4.79–4.77 (m, 1H, 3'-H), 4.42–3.83 (m, 7H, 4',5',5'-H, glycerol 1,3-H), 2.35–2.29 (m, 4H, COCH$_2$), 1.61–1.59 (m, 4H, COCCH$_2$), 1.27 (m, 56H, stearoyl CH$_2$), 0.89 (t, 6H, CH$_3$)

EXAMPLE 4

5'-(1,2-Dimyristoyl-sn-glycero-3-phospho)-2'-deoxy-2'-methylidenecytidine Sodium Salt ¾ Hydrate Using 2.0 g (2.9 mmol) of 1,2-dimyristoyl-sn-glycero-3-phosphocholine (DMPC) as phosphatidylcholine, the object compound (1.5 g) was synthesized according to the above-mentioned method, yield 59%.

Elemental analysis (C$_{41}$H$_{71}$N$_3$O$_{11}$PNa . ¾ H$_2$O) Calculated C: 57.97, H: 8.60, N: 4.95 Found C: 57.99, H: 8.83, N: 4.91

NMR (CDCl$_3$—CD$_3$OD, 3:1) δ; 7.54 (d, 1H, 6-H, J$_{6,5}$=7.6 Hz), 6.63 (s, 1H, 1'-H), 5.86 (d, 1H, 5-H, J$_{5,6}$=7.6 Hz), 5.52 (s, 1H, —C=CHa), 5.39 (s, 1H, —C=CHb), 5.23–5.22 (m, 1H, glycerol 2-H), 4.71–4.68 (m, 1H, 3'-H), 4.41–3.82 (m, 7H, 4',5',5'-H, glycerol 1,3-H), 2.34–2.28 (m, 4H, COCH$_2$), 1.60–1.59 (m, 4H, COCCH$_2$), 1.26 (m, 40H, myristoyl CH$_2$), 0.88 (t, 6H, CH$_3$)

EXAMPLE 5

5'-(1,2-Dioleoyl-sn-glycero-3-phospho)-2'-deoxy-2'-methylidenecytidine Sodium Salt ½ Hydrate Using 1.8 g (2.3 mmol) of 1,2-dioleoyl-sn-glycero-3-phosphocholine (DOPC) as phosphatidylcholine, a powdery object compound (1.6 g) was synthesized according to the above-mentioned method, yield 77%.

Elemental analysis (C$_{49}$H$_{83}$N$_3$O$_{11}$PNa . ½ H$_2$O) Calculated C: 61.74, H: 8.88, N: 4.41 Found C: 61.77, H: 8.93, N: 4.11

NMR (CDCl$_3$—CD$_3$OD, 3:1) δ; 7.62 (d, 1H, 6-H, J$_{6,5}$=7.8 Hz), 6.66 (s, 1H, 1'-H), 5.99 (d, 1H, 5-H, J$_{5,6}$=7.8 Hz), 5.51 (s, 1H, —C=CHa), 5.42 (s, 1H, —C=CHb), 5.39–5.30 (m, 4H, —CH=CH—), 5.24–5.22 (m, 1H, glycerol 2-H), 4.74–4.72 (m, 1H, 3'-H), 4.42–3.81 (m, 7H, 4',5',5'-H, glycerol 1,3-H), 2.35–2.29 (m, 4H, COCH$_2$), 2.02–1.99 (m, 8H, —CH$_2$C=CCH$_2$—), 1.61–1.60 (m, 4H, COCCH$_2$), 1.30–1.27 (m, 40H, oleoyl CH$_2$), 0.89 (t, 6H, CH$_3$)

EXAMPLE 6

5'-(1,2-Dilinoleoyl-sn-glycero-3-phospho)-2'-deoxy-2'-methylidenecytidine Sodium Salt Using 1.8 g (2.3 mmol) of 1,2-dilinoleoyl-sn-glycero-3-phosphocholine (DLPC) as phosphatidylcholine, a powdery object compound (1.8 g) was synthesized according to the above-mentioned method, yield 84%.

NMR (CDCl$_3$—CD$_3$OD, 3:1) δ; 7.55 (d, 1H, 6-H, J$_{6,5}$=7.6 Hz), 6.64 (s, 1H, 1'-H), 5.85 (d, 1H, 5-H, J$_{5,6}$=7.6 Hz), 5.52 (s, 1H, —C=CHa), 5.42–5.28 (m, 9H, —C=CHb, —CH=CH—), 5.26–5.20 (m, 1H, glycerol 2-H), 4.71–4.68 (m, 1H, 3'-H), 4.42–3.81 (m, 7H, 4',5',5'-H, glycerol 1,3-H), 2.77 (t, 4H, C=C—CH$_2$—C=C), 2.35–2.28 (m, 4H, COCH$_2$), 2.08–2.02 (m, 8H, —CCH$_2$C=C—), 1.61–1.59 (m, 4H, COCCH$_2$), 1.39–1.22 (m, 28H, linoleoyl CH$_2$), 0.89 (t, 6H, CH$_3$)

EXAMPLE 7

5'-(1,2-O-Dipalmityl-sn-glycero-3-phospho)-2'-deoxy-2'-methylidenecytidine Sodium Salt Monohydrate Using 0.50 g (0.7 mmol) of 1,2-O-dipalmityl-sn-glycero-3-phosphocholine as phosphatidylcholine, a powdery object compound (0.41 g) was synthesized according to the above-mentioned method, yield 65%.

Elemental analysis (C$_{45}$H$_{83}$N$_3$O$_9$PNa . H$_2$O) Calculated C: 61.27, H: 9.71, N: 4.76 Found C: 61.23, H: 9.52, N: 4.46

FAB-MS (m/z); 864 (M$^+$)

EXAMPLE 8

5'-(1,2-O-Distearyl-sn-glycero-3-phospho)-2'-deoxy-2'-methylidenecytidine Sodium Salt ½ Hydrate Using 0.50 g (0.7 mmol) of 1,2-O-distearyl-sn-glycero-3-phosphocholine as phosphatidylcholine, a powdery object compound (0.38 g) was synthesized according to the above-mentioned method, yield 62%.

Elemental analysis (C$_{49}$H$_{91}$N$_3$O$_9$PNa . ½ H$_2$O) Calculated C: 63.34, H: 9.98, N: 4.52 Found C: 63.53, H: 9.72, N: 4.35

FAB-MS (m/z); 920 (M$^+$)

In Examples 9 to 13, the following method was used.

2'-Deoxy-2'-methylidene-5-fluorocytidine (0.65–0.73 g, 2.5–2.8 mmol) and sodium acetate (0.2 g) were dissolved in purified water (10 ml). The pH of the mixture was adjusted to 4.3–4.5 with 1N hydrochloric acid. PLDP (1–3 mg, 180–540 U) and phosphatidylcholine (1.0–1.5 mmol) dissolved in 20 ml of chloroform were added, and the mixture was vigorously stirred at 35°–40° C. for 3–20 hours. The reaction mixture was partitioned between chloroform (13 ml) and methanol (16 ml), and the lower layer was washed by adding methanol (16 ml) and water (10 ml). The solvent was distilled away. The residue was dissolved in a small amount of chloroform-methanol (2:1) and adsorbed on silica gel, which was purified by silica gel column chromatography (eluted with chloroform:methanol=3:1) to give a white solid. The solid was dissolved in a chloroform:methanol solution (2:1, 180 ml) and the mixture was partitioned from 0.75N hydrochloric acid (27 ml). Water (27 ml) and methanol (30 ml) were added to the lower layer to partition same (3 times), and methanol (30 ml) was added. The mixture was poured on Diaion WK-20 resin column (Na type) and eluted with chloroform-methanol-water (10:5:1). The solvent was distilled away and acetone was added to the residue to give a powdery object compound.

EXAMPLE 9

5'-(1,2-Distearoyl-sn-glycero-3-phospho)-2'-deoxy-2'-methylidene-5-fluorocytidine Sodium Salt ½ Hydrate Using 1.0 g (1.2 mmol) of 1,2-distearoyl-sn-glycero-3-phosphocholine (DSPC) as phosphatidylcholine, a powdery object compound (0.31 g) was synthesized according to the above-mentioned method, yield 25%.

Elemental analysis ($C_{49}H_{86}N_3O_{11}$ FPNa . ½ $H_2O$) Calculated C: 59.26, H: 9.03, N: 4.23 Found C: 59.28, H: 9.02, N: 4.06

NMR ($CDCl_3$—$CD_3OD$, 3:1) δ; 7.67 (d, 1H, 6-H, $J_{6,5F}$= 5.9 Hz), 6.62 (s, 1H, 1'-H), 5.54 (s, 1H, —C=CHa), 5.45 (s, 1H, —C=CHb), 5.26–5.22 (m, 1H, glycerol 2-H), 4.72–4.69 (m, 1H, 3'-H), 4.42–3.81 (m, 7H, 4',5',5'-H, glycerol 1,3-H), 2.35–2.28 (m, 4H, $COCH_2$), 1.61–1.59 (m, 4H, $COCCH_2$), 1.26 (m, 56H, stearoyl $CH_2$), 0.88 (t, 6H, $CH_3$)

EXAMPLE 10

5'-(1,2-Dimyristoyl-sn-glycero-3-phospho)-2'-deoxy-2'-methylidene-5-fluorocytidine Sodium Salt Monohydrate Using 1.0 g (1.5 mmol) of 1,2-dimyristoyl-sn-glycero-3-phosphocholine (DMPC) as phosphatidylcholine, a powdery object compound (0.33 g) was synthesized according to the above-mentioned method, yield 26%.

Elemental analysis ($C_{41}H_{70}N_3O_{11}$ FPNa . $H_2O$) Calculated C: 56.47, H: 8.32, N: 4.82 Found C: 56.35, H: 8.18, N: 4.75

NMR ($CDCl_3$—$CD_3OD$, 3:1) δ; 7.65 (d, 1H, 6-H, $J_{6,5F}$= 6.3 Hz), 6.62 (s, 1H, 1'-H), 5.55 (s, 1H, —C=CHa), 5.44 (s, 1H, —C=CHb), 5.26–5.22 (m, 1H, glycerol 2-H), 4.71–4.68 (m, 1H, 3'-H), 4.42–3.82 (m, 7H, 4',5',5'-H, glycerol 1,3-H), 2.35–2.28 (m, 4H, $COCH_2$), 1.61–1.59 (m, 4H, $COCCH_2$), 1.26 (m, 40H, myristoyl $CH_2$), 0.88 (t, 6H, $CH_3$)

EXAMPLE 11

5'-(1,2-Dioleoyl-sn-glycero-3-phospho)-2'-deoxy-2'-methylidene-5-fluorocytidine Sodium Salt ½ Hydrate Using 0.8 g (1.0 mmol) of 1,2-dioleoyl-sn-glycero-3-phosphocholine (DOPC) as phosphatidylcholine, a powdery object compound (0.32 g) was synthesized according to the above-mentioned method, yield 33%.

Elemental analysis ($C_{49}H_{82}N_3O_{11}$ FPNa . ½ $H_2O$) Calculated C: 60.60, H: 8.61, N: 4.33 Found C: 60.46, H: 8.65, N: 4.08

NMR ($CDCl_3$—$CD_3OD$, 3:1) δ; 7.63 (d, 1H, 6-H, $J_{6,5F}$= 5.9 Hz), 6.61 (s, 1H, 1'-H), 5.55 (s, 1H, —C=CHa), 5.43 (s, 1H, —C=CHb), 5.39–5.29 (m, 4H, —CH=CH—), 5.25–5.21 (m, 1H, glycerol 2-H), 4.70–4.67 (m, 1H, 3'-H), 4.42–3.81 (m, 7H, 4',5',5'-H, glycerol 1,3-H), 2.35–2.28 (m, 4H, $COCH_3$), 2.03–2.00 (m, 8H, —$CH_2C$=$CCH_2$—), 1.61–1.59 (m, 4H, $COCCH_2$), 1.31–1.27 (m, 40H, oleoyl $CH_2$), 0.88 (t, 6H, $CH_3$)

EXAMPLE 12

5'-(1,2-Dilinoteoyl-sn-glycero-3-phospho)-2'-deoxy-2'-methylidene-5-fluorocytidine Sodium Salt Dihydrate Using 0.8 g (1.0 mmol) of 1,2-dilinoleoyl-sn-glycero-3-phosphocholine (DLPC) as phosphatidylcholine, a powdery object compound (0.31 g) was synthesized according to the above-mentioned method, yield 31%.

NMR ($CDCl_3$—$CD_3OD$, 3:1) δ; 7.66 (d, 1H, 6-H, $J_{6,5F}$= 5.9 Hz), 6.62 (s, 1H, 1'-H), 5.54 (s, 1H, —C=CHa), 5.45 (s, 1H, —C=CHb), 5.42–5.29 (m, 8H, —CH=CH—), 5.27–5.22 (m, 1H, glycerol 2-H), 4.71–4.68 (m, 1H, 3'-H), 4.42–3.80 (m, 7H, 4',5',5'-H, glycerol 1,3-H), 2.77 (t, 4H, C=C—$CH_2$—C=C), 2.35–2.28 (m, 4H, $COCH_2$), 2.08–2.02 (m, 8H, —$CCH_2C$=C—), 1.61–1.60 (m, 4H, $COCCH_2$), 1.39–1.24 (m, 28H, linoleoyl $CH_2$), 0.89 (t, 6H, $CH_3$)

EXAMPLE 13

5'-(1,2-O-Dipalmityl-sn-glycero-3-phospho)-2'-deoxy-2'-methylidene-5-fluorocytidine Sodium Salt ½ Hydrate Using 0.25 g (0.35 mmol) of 1,2-O-dipalmityl-sn-glycero-3-phosphocholine as phosphatidylcholine, a powdery object compound (0.09 g) was synthesized according to the above-mentioned method, yield 29%.

Elemental analysis ($C_{45}H_{82}N_3O_9$ FPNa . ½ $H_2O$) Calculated C: 60.65, H: 9.39, N: 4.72 Found C: 60.73, H: 9.30, N: 4.48

FAS-MS (m/z); 882 ($M^+$)

EXPERIMENTAL EXAMPLE 1

A compound was dissolved in dimethyl sulfoxide and serially diluted with injectable distilled water up to 20-fold diluted final concentration to give test solutions having a concentration of 1.0, 0.5, 0.125 or 0.0625 µg/ml. The test solutions (10 µl) were placed in 96 well microculture plates (Falcon No. 3072), and L1210 leukemia cell suspension (190 µl, 1×10⁵ cells/ml) was added. The mixture was incubated in a $CO_2$ gas incubator at 37° C. for 48 hours. As a control, cultures incubated in the same manner but containing 10 µl of injectable distilled water alone were used.

After the incubation, viable cells were counted using an erythrocyte counter according to the trypan blue stain method, and 50% tumor growth inhibition ratio ($IC_{50}$, µg/ml) was determined.

EXPERIMENTAL EXAMPLE 2

P388 Leukemia cells (10⁶ cells, obtained from US National Institute of Cancer) were intraperitoneally transplanted to female $CDF_1$ mice (8 weeks of age, 3 per group), and the compound was intraperitoneally administered once a day for 5 consecutive days from the next day of the transplantation. Median survival time (MST) was determined, based on which life prolonging ratio (T/C, %) was calculated from the following equation.

$$\text{Life prolonging ratio } (T/C, \%) = \frac{MST \text{ of treated group}}{MST \text{ of control group}} \times 100$$

EXPERIMENTAL EXAMPLE 3

Human LX-1 lung cancer tumor fragment (2×2×2 mm) was subcutaneously implanted in the back of BALB/C-nu/nu mice. When the volume of the tumor became 100–500 $mm^3$, the mice were divided into several test groups of 4 or 5 mice per group. The test compound was administered once a day for 5 days. The diameter of the tumor was measured and the volume (V) of the tumor was calculated from the following equation $$V = \frac{L \times W^2}{2}$$

wherein L and W are the major axis and the minor axis of the tumor (mm), respectively. The volume of the tumor in each mouse was calculated and tumor volume ratio $V_n/V_0$ is given. As used herein, $V_n$ is the tumor volume after administration of the test compound for n days and $V_0$ is the initial volume of the tumor before administration of the test compound (Day 0). $V_n/V_0$ (RV) was calculated with respect to each group and efficacy was calculated from the following equation.

$$\text{Efficacy } (T/C, \%) = \frac{RV \text{ of treated group}}{RV \text{ of control group}} \times 100$$

In this experiment, the tumor volume was measured at the 7th day from the initial administration, and antitumor effect (tumor growth-inhibitory effect) of respective compounds was studied.

FORMULATION EXAMPLE 1

Tablets containing:

| Compound of the invention | 30.0 mg |
|---|---|
| Finely divided cellulose | 25.0 mg |
| Lactose | 39.5 mg |
| Starch | 40.0 mg |
| Talc | 5.0 mg |
| Magnesium stearate | 0.5 mg |

When desired, the tablets can be prepared into sugar-coated tablets or film-coated tablets by applying sugar coating or film coating treatment.

FORMULATION EXAMPLE 2

Capsules containing the ingredients of:

| Compound of the invention | 30.0 mg |
|---|---|
| Lactose | 40.0 mg |
| Starch | 15.0 mg |
| Talc | 5.0 mg |

FORMULATION EXAMPLE 3

Fine powder containing:

| Compound of the invention | 10% |
|---|---|
| Lactose | 80% |
| Starch | 10% |

FORMULATION EXAMPLE 4

Granules containing:

| Compound of the invention | 10% |
|---|---|
| Lactose | 55% |
| Finely divided cellulose | 20% |
| Starch | 15% |

FORMULATION EXAMPLE 5

| Compound of the invention | 30.0 mg |
|---|---|
| Glucose | 100.0 mg |

The above ingredients are dissolved in purified water to give an injection (total amount 2 ml).

FORMULATION EXAMPLE 6

Suppository containing:

| Compound of the invention | 100 mg |
|---|---|
| Witepsol® H15 | 950 mg |
| Witepsol® E75 | 950 mg |

Note that Witepsol is a trademark owned by Witten A-G (Germany).

FORMULATION EXAMPLE 7

| Compound of the invention | 2 g |
|---|---|
| Ethyl p-hydroxybenzoate | 0.025 g |
| Propyl p-hydroxybenzoate | 0.015 g |
| Sodium laurylsulfate | 1.5 g |
| Propylene glycol | 12.0 g |
| Stearyl alcohol | 22.0 g |
| White soft paraffin | 25.0 g |

The above ingredients are dissolved in purified water to give a hydrophilic ointment (total amount 100.0 g).

What is claimed is:

1. A 2'-methylidenenucleotide compound of the formula (I)

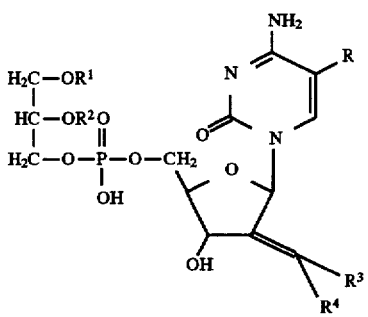

(I)

wherein

R is a hydrogen or a halogen;

$R^1$ and $R^2$ are the same or different and each is a fatty acid residue or a hydrocarbon residue; and $R^3$ and $R^4$ are the same or different and each is a hydrogen, a halogen or an alkyl, or a salt thereof.

2. The 2'-methylidenenucleotide compound of claim 1, wherein R, $R^3$ and $R^4$ are each hydrogen, or a salt thereof.

3. The 2'-methylidenenucleotide compound of claim 1, wherein R is fluorine, and $R^3$ and $R^4$ are each hydrogen, or a salt thereof.

4. The 2'-methylidenenucleotide compound of claim 1, wherein R, $R^3$ and $R^4$ are each hydrogen, and $R^1$ and $R^2$ are the same fatty acid residues, or a salt thereof.

5. The 2'-methylidenenucleotide compound of claim 1, wherein R is fluorine, $R^3$ and $R^4$ are each hydrogen, and $R^1$ and $R^2$ are the same fatty acid residues, or a salt thereof.

6. The 2'-methylidenenucleotide compound of claim 1, wherein R, $R^3$ and $R^4$ are each hydrogen, and $R^1$ and $R^2$ are the same fatty acid residues having 12 to 20 carbon atoms, or a salt thereof.

7. The 2'-methylidenenucleotide compound of claim 1, wherein R is fluorine, $R^3$ and $R^4$ are each hydrogen, and $R^1$ and $R^2$ are the same fatty acid residues having 12 to 20 carbon atoms, or a salt thereof.

8. A method for producing a 2'-methylidenenucleotide compound of claim 1 or a salt thereof, comprising reacting a phospholipid of the formula (II)

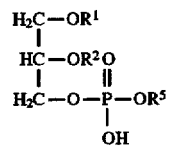

(II)

wherein $R^1$ and $R^2$ are as defined in claim 1, and $R^5$ is a choline residue, with a nucleoside of the formula (III)

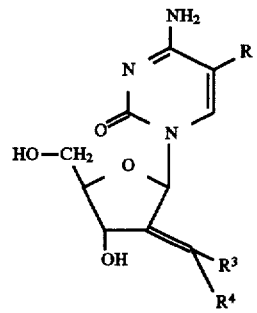

(III)

wherein R, $R^3$ and $R^4$ are as defined in claim 1, in the presence of a phospholipase D.

9. A pharmaceutical composition comprising a 2'-methylidenenucleotide compound of any one of claim 1 to claim 7 or a salt thereof, and a pharmaceutically acceptable carrier.

10. A method for treating a tumor, comprising administering an effective amount of a 2'-methylidenenucleotide compound of any one of claim 1 to claim 7 or a salt thereof to a mammal inclusive of a human host in need of treatment, wherein said tumor is sensitive to said compound.

* * * * *